(12) United States Patent
Capaldi et al.

(10) Patent No.: US 9,758,521 B2
(45) Date of Patent: Sep. 12, 2017

(54) KINASE INHIBITORS

(71) Applicant: CHIESI FARMACEUTICI S.P.A., Parma (IT)

(72) Inventors: Carmelida Capaldi, Parma (IT); Elisabetta Armani, Parma (IT); Andrew Steven Robert Jennings, Harlow (GB); Christopher Hurley, Harlow (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/388,178

(22) Filed: Dec. 22, 2016

(65) Prior Publication Data

US 2017/0183344 A1    Jun. 29, 2017

(30) Foreign Application Priority Data

Dec. 23, 2015 (EP) .................................... 15202350

(51) Int. Cl.
*A61K 31/44* (2006.01)
*C07D 471/04* (2006.01)

(52) U.S. Cl.
CPC .................. *C07D 471/04* (2013.01)

(58) Field of Classification Search
CPC ..................................................... C07D 471/04
USPC ........................................................... 514/303
See application file for complete search history.

(56) References Cited

U.S. PATENT DOCUMENTS

| | | | | |
|---|---|---|---|---|
| 8,907,094 B2* | 12/2014 | Van Niel | ............. | C07D 401/12 546/119 |
| 9,139,584 B2* | 9/2015 | Van Niel | ............. | C07D 401/12 |
| 9,359,354 B2* | 6/2016 | Woo | .................... | C07D 471/10 |
| 9,573,949 B2* | 2/2017 | Alcaraz | ................ | C07D 519/00 |

FOREIGN PATENT DOCUMENTS

| | | |
|---|---|---|
| WO | 2013/083604 | 6/2013 |
| WO | 2014/195400 | 12/2014 |

OTHER PUBLICATIONS

International Search Report in Application No. PCT/EP2016/081839 issued Feb. 20, 2017.
European Search Report in Application No. 15202350.3 dated Mar. 17, 2016.

* cited by examiner

*Primary Examiner* — Nizal Chandrakumar
(74) *Attorney, Agent, or Firm* — Oblon, McClelland, Maier & Neustadt, L.L.P.

(57) ABSTRACT

Compounds of formulae (I), (II), and (III), defined herein, are p38 MAPK inhibitors and are useful as anti-inflammatory agents in the treatment of, inter alia, diseases of the respiratory tract.

7 Claims, No Drawings

KINASE INHIBITORS

CROSS REFERENCES TO RELATED APPLICATIONS

This application claims priority to European Patent Application No. 15202350.3 filed on Dec. 23, 2015, which is incorporated herein by reference in its entirety.

BACKGROUND OF THE INVENTION

Field of the Invention

The present invention relates to compounds and compositions which are p38 MAPK inhibitors and are useful as anti-inflammatory agents in the treatment of, inter alia, diseases of the respiratory tract.

Discussion of the Background

Mitogen activated protein kinases (MAPK) constitute a family of proline-directed serine/threonine kinases that activate their substrates by dual phosphorylation. There are four known human isoforms of p38 MAP kinase, p38α, p38β, p38γ, and p38δ. The p38 kinases, which are also known as cytokine suppressive anti-inflammatory drug binding proteins (CSBP), stress activated protein kinases (SAPK) and RK, are responsible for phosphorylating (see Stein et al., Ann. Rep. Med Chem., 1996, 31, 289-298, which is incorporated herein by reference in its entirety) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (see Herlaar E. & Brown Z., Molecular Medicine Today, 1999, 5, 439-447, which is incorporated herein by reference in its entirety). The products of p38 phosphorylation have been shown to mediate the production of inflammatory cytokines, including tumor necrosis factor alpha (TNF α) and interleukin-(IL)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (see, e.g., Dinarello et al., Rev. Infect. Disease, 1984, 6, 51, which is incorporated herein by reference in its entirety). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (see Badger et al., J. Pharm. Exp. Thera., 1996, 279, 1453-1461; Griswold et al, Pharmacol. Comm.,1996, 7, 323-229, which are incorporated herein by reference in their entireties). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α, IL-1β, IL-6, IL-4, IL-5 and IL-13 (see Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288, all of which are incorporated herein by reference in their entireties). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (see Lee et al., Immunopharmacology, 2000, 47, 185-200, which is incorporated herein by reference in its entirety). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425, which is incorporated herein by reference in its entirety). It is believed that the compounds of the present invention can be used to treat p38 mediated diseases such as: chronic obstructive pulmonary disease (COPD), asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (non-malignant) conditions, such as hemangiomas, angiofibroma of the nasopharynx, and avascular necrosis of bone, benign and malignant tumors/neoplasia including cancer, leukaemia, lymphoma, systemic lupus erythematosus, angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1, herpes simplex virus type-2, cytomegalovirus, varicella-zoster virus, Epstein-Barr virus, human herpes virus-6, human herpesvirus-7, human herpesvirus-8, pseudorabies and rhino-tracheitis, among others.

Known P38 kinase inhibitors have been reviewed by G. J. Hanson (Expert Opinions on Therapeutic Patents, 1997, 7, 729-733, which is incorporated herein by reference in its entirety) J Hynes et al. (Current Topics in Medicinal Chemistry, 2005, 5, 967-985, which is incorporated herein by reference in its entirety), C. Dominguez et al (Expert Opinions on Therapeutics Patents, 2005, 15, 801-816, which is incorporated herein by reference in its entirety) and L. H. Pettus & R. P. Wurtz (Current Topics in Medicinal Chemistry, 2008, 8, 1452-1467, which is incorporated herein by reference in its entirety). P38 kinase inhibitors are known, for example WO2014/195400 and WO 2013/083604, both of which are incorporated herein by reference in their entireties.

However, there remains a need for improved kinase inhibitors for the treatment of diseases of the respiratory tract.

SUMMARY OF THE INVENTION

Accordingly, it is one object of the present invention to provide novel kinase inhibitors.

It is another object of the present invention to provide novel p38 MAPK inhibitors.

It is another object of the present invention to provide novel p38 MAPK inhibitors which are useful as anti-inflammatory agents in the treatment of, inter alia, diseases of the respiratory tract.

It is another object of the present invention to provide novel methods of treating of, inter alia, diseases of the respiratory tract.

Another object of the invention is to identify novel potent p38 mitogen activated protein kinase inhibitors which show an appropriate developability profile on inhalatory administration to effectively treat respiratory obstructive or inflammatory diseases. It is to be understood that such profile may be achieved in a number of different ways by modulation of specific properties; by way of example, it could be achieved by administration of a low effective dose of the drug thus limiting side effects or via a long duration of action in the lungs which may reduce the frequency of administration.

These and other objects, which will become apparent during the following detailed description, have been achieved by the inventors' discovery that compounds of formulae (I), (II), and (III) described below are inhibitors of p38 mitogen activated protein kinase ("p38 MAPK," "p38 kinase," or "p38"), including p38α kinase, and are inhibitors of cytokine and chemokine production including TNFα and IL-8 production.

Thus, the compounds of the present invention are inhibitors of p38 mitogen activated protein kinase ("p38 MAPK," "p38 kinase," or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease and asthma. They are therefore particularly suited for pulmonary delivery, by inhalation by nose or mouth.

Like the known compounds, the present compounds are useful for the treatment of diseases of the respiratory tract.

However, the present compounds have the unexpected advantage of a higher potency, maintaining a good anti-inflammatory activity.

DETAILED DESCRIPTION OF THE PREFERRED EMBODIMENTS

Thus, the present invention provides compounds of formula (I):

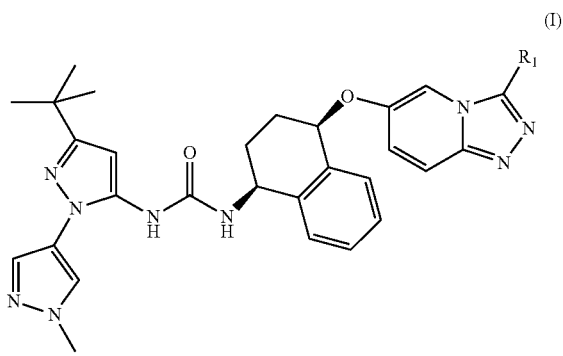

wherein
$R_1$ is selected from the group consisting of

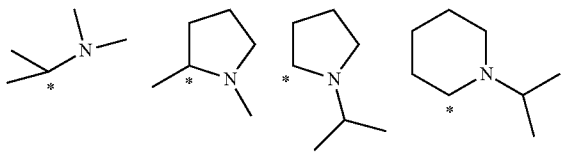

and pharmaceutically acceptable salts thereof.

The present invention also provides compounds of formula (II):

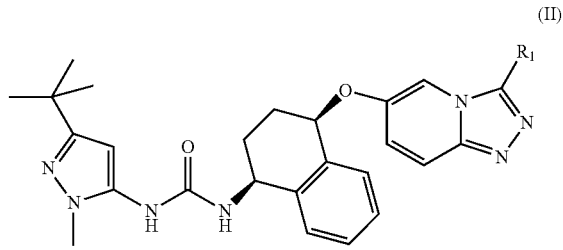

wherein
$R_1$ is selected from the group consisting of

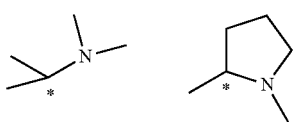

and pharmaceutically acceptable salts thereof.

The present invention also provides compounds of formula (III):

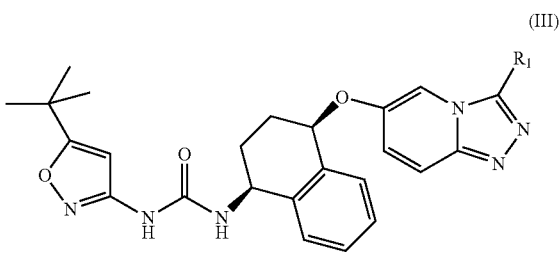

(III)

wherein
R₁ is selected from the group consisting of

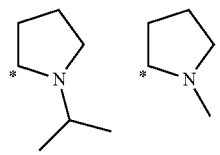

and pharmaceutically acceptable salts thereof.

The present invention also provides pharmaceutical compositions comprising a compound of the invention, together with one or more pharmaceutically acceptable carriers and/or excipients. Compositions adapted for inhalation for pulmonary administration are preferred.

The present invention further provides the use of a compound of the invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, bronchiectasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

Compounds of the present invention may exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and re-crystallization techniques). Where appropriate such isomers may be prepared by the application of adaptation of known methods (e.g. asymmetric synthesis).

Throughout the specification the use of an asterisk "*" in the definition of a structural formula, indicates the point of attachment for the radical group to the rest of the molecule.

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in several polymorphic forms and may be obtained in different crystal or co-crystal habits, and they are intended to be included within the meaning of the term "compounds of the invention".

The compounds may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and V. J. Stella) and Bioreversible Carriers in Drug Design, Pergamon Press, 1987 (ed. E. B. Roche, American Pharmaceutical Association; C. S. Larsen and J. Østergaard, Design and application of prodrugs, In Textbook of Drug Design and Discovery, 3$^{rd}$ Edition, 2002, Taylor and Francis), all of which are incorporated herein by reference in their entireties.

Prodrugs in accordance with the present invention can, for example, be produced by replacing appropriate functionalities present in the compounds of formula (I), (II) and (III) with 'pro-moieties' as described, for example, in Design of Prodrugs by H. Bundgaard (Elsevier, 1985), which is incorporated herein by reference in its entirety. Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

In one embodiment, a compound of formula (I) is selected from:
  1-(3-tert-Butyl-1'-methyl-1'H-[1,4']bipyrazolyl-5-yl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalenyl}-urea hydrochloride salt;
  1-(3-tert-Butyl-1'-methyl-1'H-[1,4']bipyrazolyl-5-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalenyl}-urea hydrochloride salt;
  1-(3-tert-Butyl-1'-methyl-1'H-[1,4']bipyrazolyl-5-yl)-3-{(1S,4R)-4-[3-((S)-1-isopropyl-pyrrolidin-2-yl)-[1,2,4]triazolo[4,3-a]pyridin-6-yloxy]-1,2,3,4-tetrahydro-naphthalenyl}-urea hydrochloride salt; and
  1-(3-tert-Butyl-1'-methyl-1'H-[1,4']bipyrazolyl-5-yl)-3-{(1S,4R)-4-[3-((S)-1-isopropyl-piperidin-2-yl)-[1,2,4]triazolo[4,3-a]pyridin-6-yloxy]-1,2,3,4-tetrahydro-naphthalen-1-yl}-urea hydrochloride salt.

In another embodiment, a compound of formula (II) is selected from:
  1-(5-tert-Butyl-2-methyl-2H-pyrazol-3-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea hydrochloride salt; and 1-(5-tert-Butyl-2-methyl-2H-pyrazol-3-yl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea hydrochloride salt.

In another embodiment, a compound of formula (III) is selected from:

1-(5-tert Butyl-isoxazol-3-yl)-3-{(1S,4R)-4-[3-((S)-1-isopropyl-pyrrolidin-2-yl)-[1,2,4]triazolo[4,3-a]pyridine-6-yloxy]-1,2,3,4-tetrahydronaphthalen-1-yl}-urea hydrochloride salt; and 1-(5-tert Butyl-isoxazol-3-yl)-3-{(1S,4R)-4-[3-((S)-1-methyl-pyrrolidin-2-yl)-[1,2,4]triazolo[4,3-a]pyridine-6-yloxy]-1,2,3,4-tetrahydronaphthalen-1-yl}-urea hydrochloride salt.

As mentioned above the compounds of the invention are p38MAPK inhibitors, and thus may have utility for the treatment of diseases or conditions which benefit from inhibition of the p38 enzyme. Such diseases and conditions are known and several have been mentioned above. However, the compounds are generally used as anti-inflammatory agents, particularly for use in the treatment of respiratory disease. In particular, the compounds may be used in the treatment of chronic obstructive pulmonary disease, chronic bronchitis, lung fibrosis, pneumonia, acute respiratory distress syndrome, pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

The present invention provides the use of the compounds of the invention for the prevention and/or treatment of any disease or condition which benefit from inhibition of the p38 enzyme.

In a further aspect the present invention provides the use of compounds of the invention for the preparation of a medicament for the prevention and/or treatment of any disease or condition which benefit from inhibition of the p38 enzyme.

Moreover the present invention provides a method for prevention and/or treatment of any disease which benefit from inhibition of the p38 enzyme, said method comprises administering to a patient in need of such treatment a therapeutically effective amount of a compound of the invention.

As mentioned above, the compounds of the invention are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases. For the purpose of the invention, inhaled administration is preferred.

The compounds of the invention may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricants, for example magnesium stearate, talc, polyethylene glycol or silica; disintegrants for example potato starch, or acceptable wetting agents such as sodium lauryl sulfate. The tablets may be coated according to known methods. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerin, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations which may be used for the drug are conventional formulations, for example described in standard textbooks of pharmaceutics such as the British Pharmacopoeia, which is incorporated herein by reference in its entirety.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronization. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebulizer or as an aerosol in a liquid propellant, for example for use in a pressurized metered dose inhaler (PMDI). Propellants suitable for use in a PMDI are known to the skilled person, and include CFC-12, HFA-134a, HFA-227, HCFC-22 and HFA-152.

A composition of the present invention is preferably in dry powder form, for delivery using a dry powder inhaler (DPI). Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm. In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0 505 321, which is incorporated herein by reference in its entirety). Additionally, compounds of the invention may be delivered in multi-chamber devices thus allowing for delivery of combination agents.

Other compounds may be combined with compounds of the invention for the prevention and treatment of inflammatory diseases, in particular respiratory diseases. Thus, the present invention also provides pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, formoterol/beclometasone dipropionate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028, EP-101; (5) dual pharmacology M3-anticholinergic/β2-adrenoreceptor agonists such as GSK961081, AZD2115 and LAS190792; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723, or selective histamine-4 (H4) receptor antagonists, such as ZPL3893787; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonuclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289, both of which are incorporated herein by reference in their entireties; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO2005/026124, WO2003/053930 and WO06/082412, all of which are incorporated herein by reference in their entireties; (20) A2b antagonists such as those described in WO2002/42298, which is incorporated herein by reference in its entirety; (21) modulators of chemokine receptor function, for example antagonists of CCR3 and CCR8; (22) compounds which modulate the action of other prostanoid receptors, for example a thromboxane $A_2$ antagonist; DP1 antagonists such as MK-0524, CRTH2 antagonists such as ODC9101 and OC000459 and AZD1981 and mixed DP1/CRTH2 antagonists such as AMG 009 and AMG853; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176, both of which are incorporated herein by reference in their entireties; (26) CXCR2 or IL-8 antagonists such as SCH 527123 or GSK 656933; (27) IL-R signaling modulators such as kineret and ACZ 885; and (28) MCP-1 antagonists such as ABN-912.

The present invention also provides kits comprising the pharmaceutical compositions of the invention and a device which may be a single- or multi-dose dry powder inhaler, a metered dose inhaler or a nebulizer.

Methods of Synthesis

The present invention also provides processes for the preparation of compounds of the invention, according to general synthetic routes described in this section. In the following reaction schemes, unless otherwise indicated, the groups mentioned assume the same meaning as those reported for compounds of formula (I), (II) and (III).

The skilled person may introduce, where appropriate, suitable variations to the conditions specifically described in the experimental part in order to adapt the synthetic routes to the provision of further compounds of the invention. Such variations may include, but are not limited to, use of appropriate starting materials to generate different compounds, changes in the solvent and temperature of reactions, replacements of reactants with analogous chemical role, introduction or removal of protection/deprotection stages of functional groups sensitive to reaction conditions and reagents, as well as introduction or removal of specific synthetic steps oriented to further functionalization of the chemical scaffold.

The process described is particularly advantageous as it is susceptible of being properly modulated, through any known proper variant, so as to obtain any of the desired compounds.

Functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known (see, for a general reference, T. W. Green; Protective Groups in Organic Synthesis (Wiley, N.Y. 1981), which is incorporated herein by reference in its entirety).

Likewise, selective protection and deprotection of any of the said groups, for instance including carbonyl, hydroxyl or amino groups, may be accomplished according to known methods.

Optional salification of the compounds of formula (I), (II) and (III) may be carried out by properly converting any of the free acidic or amino groups into the corresponding pharmaceutically acceptable salts according to known methods From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

For example compounds of the invention of formula (I), (II) or (III) may be prepared according to the route illustrated in Scheme 1.

Scheme 1

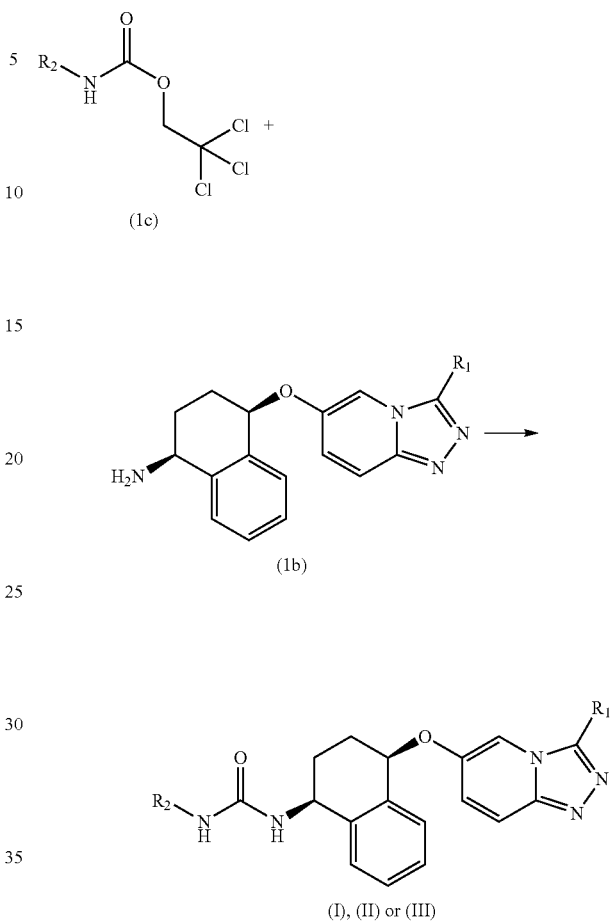

wherein $R_1$ is as defined above and $R_2$ is:

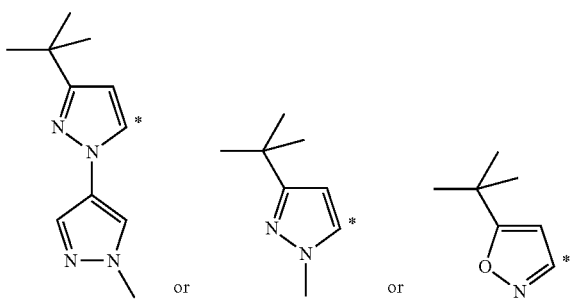

Compounds of formula (I), (II) or (III) may be prepared from compounds of formula (1b) by reaction with a compound of formula (1c) in a suitable solvent such as dimethyl sulfoxide, 1,4-dioxane, DMF, 2-methylTHF, THF or acetonitrile, in the presence of a base such as diisopropylethylamine or sodium hydroxide at a range of temperatures, preferably between room temperature and 100° C.

Compounds of formula (1c) are known (e.g. WO 2013/083604, which is incorporated herein by reference in its entirety).

Compounds of formula (1b) may be prepared according to the route illustrated in Scheme 2.

Scheme 2

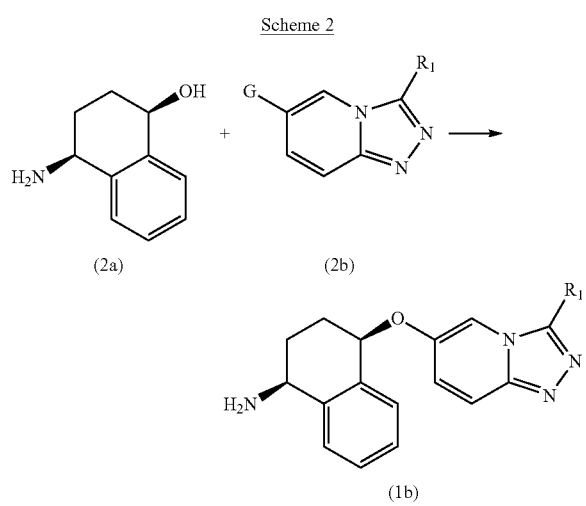

Compounds of formula (1b) may be prepared from compounds of formula (2b) by reaction with compound (2a), wherein G is a suitable known chemical group selected such that it can facilitate a suitable coupling reaction such as nucleophilic displacement or metal catalysed cross coupling. For example, G may include halogen or a suitable leaving group such as mesylate or triflate. Examples of the coupling conditions include using a base such as sodium hydride or potassium tert-butoxide and 18-crown-6 or 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between RT and 150° C.

Compounds of formula (2b) may be prepared according to the route in Scheme 3.

Compounds of formula (3e) may be prepared from compounds of formula (3a) by reaction with an aldehyde of formula (3c) in a suitable solvent such as ethanol or tetrahydrofuran at a range of temperatures, preferably between RT and 80° C.

Compounds of formula (3a) and (3c) are known or may be prepared by known methods.

Alternatively, compounds of formula (2b) may be prepared from compounds of formula (3d) using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene or NMP, at a range of temperatures, preferably between RT and 120° C.

Compounds of formula (3d) may be prepared from compounds of formula (3a) by reaction with a compound of formula (3b1) using a suitable acylating/dehydrating agent such as triphenylphosphine/trichloroacetonitrile/HOBt/2-(7-aza-1H-benzotriazole-1-yl)-1,1,3,3-tetramethyluronium hexafluorophosphate or 1-ethyl-3-(3-dimethylaminopropyl) carbodiimide in the presence of a base such as diisopropylethylamine, in a suitable solvent such as dichloromethane or acetonitrile, at a range of temperatures, preferably between RT and 150° C.

Alternatively, compounds of formula (3d) may be prepared from compounds of formula (3a) by reaction with a compound of formula (3b2) in the presence of a base such as diisopropylethylamine, in a suitable solvent such as dichloromethane or THF at a range of temperatures preferably between −10° C. and the boiling point of the solvent.

Compounds of formulae (3b1) and (3b2) are known or may be prepared by adapting appropriate known methods.

Scheme 3

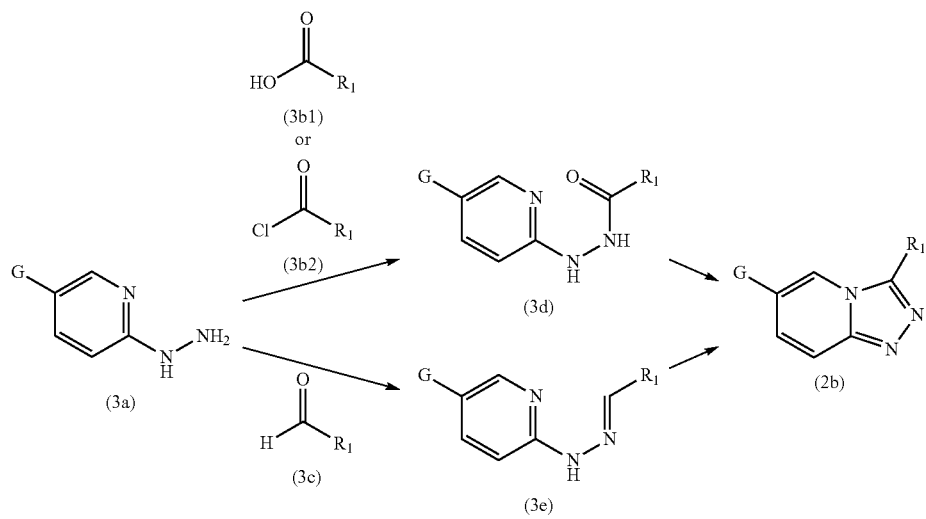

Compounds of formula (2b) may be prepared from compounds of formula (3e) as above reported using a suitable oxidant such as chloramine T, lead tetraacetate or phenyliodine(III) diacetate, in a suitable solvent such as dichloromethane or ethanol at a range of temperatures, preferably between RT and 100° C.

Compound (2a) is disclosed in WO 2013/083604, which is incorporated herein by reference in its entirety).

Other features of the invention will become apparent in the course of the following descriptions of exemplary embodiments which are given for illustration of the invention and are not intended to be limiting thereof.

EXAMPLES

General Experimental Details

Abbreviations used in the Experimental Section:
aq.=aqueous;
DCM=dichloromethane;
DIPEA=diisopropylethylamine;
DMF=N,N-dimethylformamide;
DMSO=dimethyl sulfoxide; EDC=1-ethyl-3-(3'-dimethylaminopropyl)carbodiimide hydrochloride;
EtOAc=ethyl acetate;
Et$_2$O=diethyl ether;
FCC=flash column chromatography;
h=hour;
HOBt=1-hydroxy-benzotriazole;
HPLC=high performance liquid chromatography;
IPA=propan-2-ol;
LCMS=liquid chromatography mass spectrometry;
MDAP=mass-directed auto-purification;
MeCN=acetonitrile;
MeOH=methanol;
min=minutes;
NMR=nuclear magnetic resonance;
Ph$_3$P=triphenylphosphine;
RT=room temperature;
Rt=retention time;
TFA=trifluoroacetic acid; and
THF=Tetrahydrofuran.

In the procedures that follow, after each starting material, reference to an Intermediate/Example number is usually provided. The starting material may not necessarily have been prepared from the batch referred to.

When reference is made to the use of a "similar" or "analogous" procedure, such a procedure may involve minor variations, for example reaction temperature, reagent/solvent amount, reaction time, work-up conditions or chromatographic purification conditions.

The nomenclature of structures was assigned using Autonom 2000 Name software from MDL Inc. When the nomenclature of structures could not be assigned using Autonom, ACD/Name software utility part of the ACD/Labs Release 12.00 Product Version 12.5 (Build 45133, 16 Dec. 2010) was used. Stereochemical assignments of compounds are based on comparisons with data reported in WO 2008/043019, which is incorporated herein by reference in its entirety, for key intermediates. All reactions were carried out under anhydrous conditions and an atmosphere of nitrogen or argon unless specified otherwise.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane ($\delta$=0 ppm). J values are given in Hz through-out. NMR spectra were assigned using DataChord Spectrum Analyst Version 4.0.b21 or SpinWorks version 3.

When products were purified by flash column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d. Genesis column with 7 μm particle size), or a Phenyl-Hexyl column (250×21.2 mm i.d. Gemini column with 5 μm particle size), UV detection between 220-254 nm, flow 5-20 mL/min), eluting with gradients from 100-0 to 0-100% water/acetonitrile (containing 0.1% TFA or 0.1% formic acid) or a C18-reverse-phase column (19×250 mm, XBridge OBD, with 5 μm particle size), eluting with gradients from 100-0 to 0-100% water/acetonitrile (containing 0.1% NH$_4$OH); or a ChiralPak IC column (10×250 mm i.d., with 5 μm particle size), unless otherwise indicated Fractions containing the required product (identified by LCMS analysis) were pooled, the organic solvent removed by evaporation, and the remaining aqueous residue lyophilized, to give the final product. Products purified by preparative HPLC were isolated as free base, formate or TFA salts, unless otherwise stated.

The Liquid Chromatography Mass Spectroscopy (LCMS) and HPLC systems used are:

Method 1

Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line HP1100 DAD detector). MS ionization method—Electrospray (positive and negative ion).

Method 2

Waters micromass ZQ2000 quadrupole mass spectrometer with an Acquity BEH C18 1.7 um 100×2.1 mm, Acquity BEH Shield RP18 1.7 um 100×2.1 mm or Acquity HSST3 1.8 um 100×2.1 mm, maintained at 40° C. Elution with A: water+0.1% formic acid; B: acetonitrile+0.1% formic acid. Gradient:

| Gradient - Time | flow mL/min | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 3

Agilent 1260 infinity purification system. Column: XBridge Prep C18 OBD, particle size 5 μm, 30×150 mm, RT. Elution with A: water+0.1% ammonia; B: CH$_3$CN+0.1% ammonia. Gradient—90% A/10% B to 2% A/95% B over 22 min—flow rate 60 mL/min. Detection—In-line Agilent 6100 series single Quadrupole LC/MS.

Intermediate A. (1S,4R)-4-[3-((S)-1-Dimethyl-amino-2-methyl-propyl)-[1,2,4]triazolo[4,3-a]pyridin-6-yloxy]-1,2,3,4-tetrahydro-naphthalen-1-ylamine

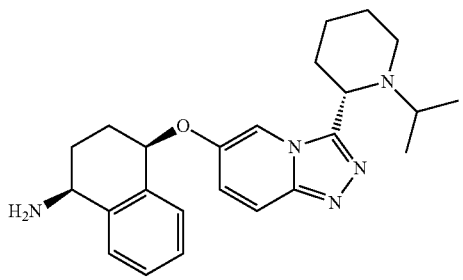 [SMILES: CC(C)N1CCCC[C@H]1c1nnc2ccc(O[C@@H]3CC[C@H](N)c4ccccc43)cn12]

a. 1-Isopropyl-piperidine-2-carboxylic acid N'-(5-fluoro-pyridin-2-yl)-hydrazide (Intermediate Aa)

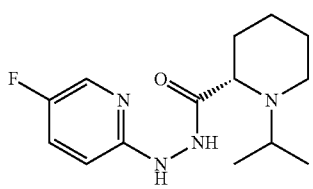 [SMILES: CC(C)N1CCCC[C@H]1C(=O)NNc1ccc(F)cn1]

A solution of 1-isopropyl-L-pipecolinic acid (CAS: 1141826-51-8, 1.41 g, 8.23 mmol) and (5-fluoro-pyridin-2-yl)-hydrazine (WO 2013/083604, 1.00 g, 7.87 mmol) in DCM (10 ml) was treated with EDC (1.65 g, 8.61 mmol) and HOBt (106 mg, 0.78 mmol). The reaction mixture was stirred overnight at RT. The reaction mixture was quenched with $H_2O$ and the two phases were separated. The aqueous phase was extracted with DCM (×2) and the combined organic phases were washed with brine, dried with $Na_2SO_4$ and the solvent was removed under reduced pressure to give the title compound (1.14 g, 52%).

LCMS (Method 1): Rt 0.45 min, m/z 281 [MH+].

b. 6-Fluoro-3-((S)-1-isopropyl-piperidin-2-yl)-[1,2,4]triazolo[3,4-a]pyridine (Intermediate Ab)

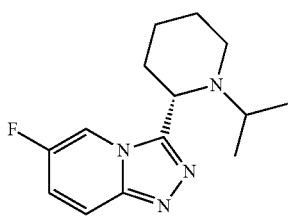 [SMILES: CC(C)N1CCCC[C@H]1c1nnc2ccc(F)cn12]

Hexachloroethane (1.92 g, 8.11 mmol) was added portion-wise to a stirred solution of Intermediate Aa (1.14 g, 4.06 mmol), triphenylphosphine (2.13 g, 8.12 mmol) and TEA (2.3 ml, 16.3 mmol) in THF (15 ml), and the reaction mixture was stirred at 55° C. for 90 minutes. The reaction mixture was cooled at RT, the solid was removed by filtration and the solvent was evaporated under reduced pressure. The residue was diluted with DCM and the organic phases were extracted with an aqueous 1M HCl solution. The aqueous phase was basified with an aqueous 1M NaOH solution. The resulting aqueous phase was extracted with DCM (×3) and the combined organic phases were dried with $Na_2SO_4$ and the solvent was removed under reduced pressure. The crude mixture was purified by FCC eluting with 0-10% 2M $NH_3$ in MeOH/DCM to give the title compound (655 mg, 62%, containing 0.15 eq of triphenylphosphine oxide).

$^1$H NMR (300 MHz, $CDCl_3$): 0.89 (3H, d, J=6.5 Hz), 1.02 (3H, d, J=6.7 Hz), 1.33-1.92 (6H, m), 2.20-2.36 (2H, m), 2.99-3.10 (1H, m), 4.32-4.42 (1H, m), 7.17 (1H, ddd, J=10.0, 7.5, 2.3 Hz), 7.41-7.76 (1H, m, NB: this signal was partially obscured by the presence of triphenylphosphine oxide impurity), 8.78 (1H, ddd, J=4.1, 2.3, 0.8 Hz).

c. Intermediate A

A stirred solution of (1R,4S)-4-amino-1,2,3,4-tetrahydro-naphthalen-1-ol (WO 2013/083604, which is incorporated herein by reference in its entirety, 405 mg, 2.48 mmol) in DMF (3 ml) under nitrogen was added with sodium hydride (60% dispersion in mineral oil, 298 mg, 7.45 mmol). The reaction mixture was stirred at RT for 20 minutes and then a solution of Intermediate Ab (0.652 g, 2.48 mmol) in DMF (3 ml) was added. The resulting mixture was stirred at 40° C. for 16 h, cooled at 0° C. and quenched with a saturated aqueous $NH_4Cl$ solution. The reaction mixture was diluted with EtOAc and brine and the two phases were separated. The aqueous phase was extracted with EtOAc (×2), the combined organic phases were dried with $Na_2SO_4$ and the solvent was removed under reduced pressure. Purification by FCC, eluting with 0-20% 2M $NH_3$ in MeOH/DCM afforded the title compound (747 mg, 74%).

$^1$H NMR (300 MHz, $CDCl_3$): 0.90 (3H, d, J=6.5 Hz), 1.03 (3H, d, J=6.5 Hz), 1.35-2.47 (13H, m), 2.95-3.05 (1H, m), 3.98 (1H, dd, J=8.5, 5.1 Hz), 4.30-4.40 (1H, m), 5.18 (1H, t, J=4.4 Hz), 7.11 (1H, dd, J=10.7, 2.3 Hz), 7.21-7.45 (4H, m), 7.59-7.67 (2H, m), 8.45 (1H, d, J=2.0 Hz).

Example 1

1-(3-tert-Butyl-1'-methyl-1'H-[1,4']bipyrazolyl-5-yl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalenyl}-urea hydrochloride salt

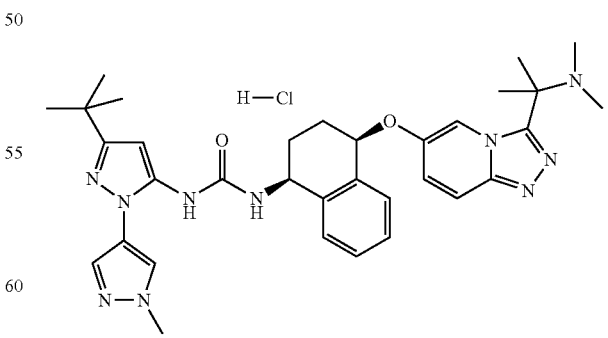

A stirred solution of (3-tert-butyl-1'-methyl-1'H-[1,4']bipyrazolyl-5-yl)-carbamic acid 2,2,2-trichloro-ethyl ester (WO 2013/083604, which is incorporated herein by reference in its entirety, 0.30 mmol), (1S,4R)-4-[3-(1-dimethylamino-1-methyl-ethyl)-[1,2,4]triazolo[4,3-a]pyridin-6-yloxy]-1,2,3,4-tetrahydro-naphthalen-1-ylamine (WO 2013/083604, which is incorporated herein by reference in its entirety, 0.27 mmol) and DIPEA (0.41 mmol) in 2-methyl-tetrahydrofuran (1 ml) was heated at 60° C. for 7 hours. The reaction mixture was diluted with 2-methyltetrahydrofuran and H₂O and the two phases were separated. The aqueous phase was extracted with 2-methyltetrahydrofuran (×2) and the combined organic phases were washed with brine, dried with Na₂SO₄ and the solvent was removed under reduced pressure. The resulting residue was purified by FCC, eluting with 0-5% 2M NH₃ in MeOH/DCM, followed by HPLC (Gemini C18, 5-95% MeCN in H₂O, 0.1% HCO₂H, 18 ml/min). The obtained solid was dissolved in MeCN (1 ml) and H₂O (1 ml) and an aqueous HCl solution (1M, 1 equivalent) was added. The mixture was lyophilized to afford the title compound (61%).

LCMS (Method 2): Rt 3.20 min, m/z 611 [MH$^+$].

$^1$H NMR (400 MHz, d-$_6$-DMSO): 1.24 (9H, s), 1.83-2.17 (10H, m), 2.58-2.85 (6H, m), 3.87 (3H, s), 4.81-4.88 (1H, m), 5.84 (1H, m), 6.27 (1H, s), 7.21 (1H, d, J=8.3 Hz), 7.43-7.27 (5H, m), 7.62 (1H, s), 7.87 (1H, d, J=9.9 Hz), 8.03 (1H, s), 8.11 (1H, s), 8.70 (1H, s), 11.3 (1H, s).

General Procedure for Examples 2-4

The compounds in Table 1 were prepared starting from (3-tert-butyl-1'-methyl-1'H-[1,4']bipyrazolyl-5-yl)-carbamic acid 2,2,2-trichloro-ethyl ester (WO 2013/083604, which is incorporated herein by reference in its entirety) and an appropriate amine using the procedure described to make Example 1.

TABLE 1

| Ex. | Amine-Intermediate | Structure | NMR (400 MHz) δ | LC-MS |
|---|---|---|---|---|
| 2 | (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety) | 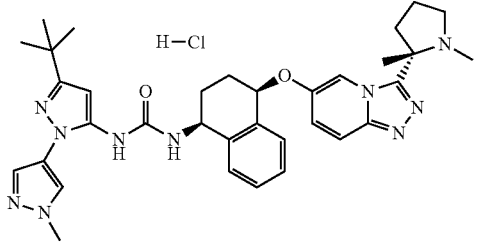 [SMILES: CN1CCC[C@@]1(C)c1nnc2ccc(O[C@@H]3CC[C@H](NC(=O)Nc4cc(C(C)(C)C)nn4-c4cnn(C)c4)c4ccccc43)cn12 ; Cl] | $^1$H NMR (400 MHz, d-$_6$-DMSO): 1.26 (9H, s), 1.59-1.52 (1H, m), 2.17-1.87 (7H, m), 2.38 (3H, s), 3.15 (1H, t, 7.8 Hz), 3.40 (3H, s), 3.85 (3H, s), 4.11 (1H, t, J = 7.7 Hz), 4.86 (1H, q, J = 4.8 Hz), 5.34 (1H, t, J = 5.1 Hz), 6.21 (1H, s), 6.89-6.96 (1H, m), 7.18-7.40 (5H, m), 7.56 (1H, s), 7.65-7.70 (1H, m), 7.83 (1H, m), 7.89 (1H, s), 8.39 (1H, m), 9.02 (1H, s). | (Method 2): Rt 3.11 min, m/z 623 [MH$^+$] |
| 3 | (1S,4R)-4-[3-((S)-1-Isopropyl-pyrrolidin-2-yl)-[1,2,4]triazolo[4,3-a]pyridin-6-yloxyl-1,2,3,4-tetrahydro-naphthalen-1-ylamine (WO 2013/083604, which is incorporated herein by reference in its entirety) | 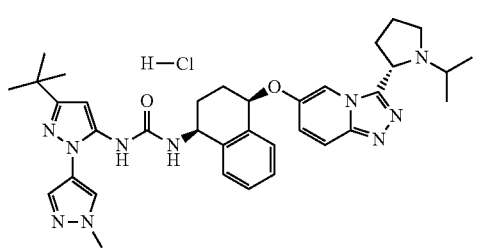 | NB. The hydrochloride salt presented two different stereoisomers due to formation of a stereogenic centre on the ammonium and the stereoisomers have been labelled with $^\#$. $^1$H NMR (400 MHz, d-$_6$-DMSO): 1.23-1.24 (15H, m), 1.81-2.36 (8H, m), 3.37-3.49 (1H, m), 3.58-3.75 (2H, m), 3.87 (3H, s), 4.82-4.90 (1H, m), 5.50-5.62 (1.7H$^\#$, m), 5.87-5.93 (0.3H$^\#$, m), 6.24-6.27 (1H, m), 7.18-7.42 (6H, m), 7.61-7.63 (1H, m), 7.85 (1H, d, J = 9.6 Hz), 8.02-8.12 (2H, m), 8.49-8.53(0.8H$^\#$, m), 8.87-8.89 (0.2H$^\#$, m), 10.32-10.50 (0.7H$^\#$, br s), 11.9-12.0 (0.3H$^\#$, m). | (Method 2): Rt 3.22 min, m/z 637 [MH$^+$] |
| 4 | Intermediate A | 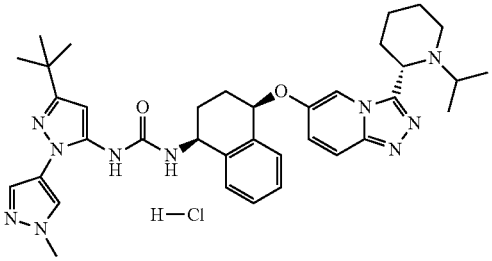 | NB. The hydrochloride salt presented two different stereoisomers due to formation of a stereogenic centre on the ammonium and the stereoisomers have been labelled with $^\#$. $^1$H NMR (400 MHz, d-$_6$-DMSO): 1.24-1.25 (15H, m), 1.66-2.36 (10H, m), 2.95-3.09 (2H, m), 3.52-3.59 (1H, m), 3.87 (3H, s), 4.82-4.90 (1H, m), 5.48-5.61 (1.9H$^\#$, m), 5.87-5.93 (0.1H$^\#$, m), 6.24-6.27 (1H, m), 7.17-7.41 (6H, m), 7.60-7.64 (1H, m), 7.82-7.89 (1H, m), 8.01-8.12 (2H, m), 8.68-8.78 (1H, m), 10.01-10.33 (0.8H$^\#$, br), 11.0-11.1 (0.2H$^\#$, m). | (Method 2): Rt 3.25 min, m/z 651 [MH$^+$] |

Examples 5

1-(5-tert-Butyl-2-methyl-2H-pyrazol-3-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea hydrochloride salt

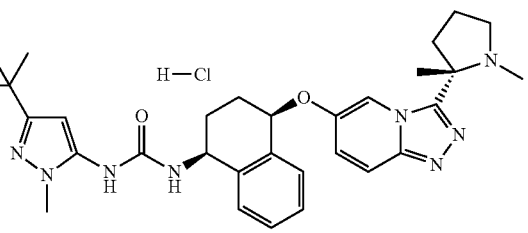

A stirred solution of (5-tert-butyl-2-methyl-2H-pyrazol-3-yl)-carbamic acid 2,2,2-trichloro-ethyl ester (WO 2013/083604, 0.47 mmol), (1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 0.42 mmol) and DIPEA (0.64 mmol) in 2-methyltetrahydrofuran (2 ml) was heated at 60° C. for 18 h. The reaction mixture was diluted with 2-methyltetrahydrofuran and H$_2$O and the two phases were separated. The aqueous phase was extracted with 2-methyltetrahydrofuran (×2) and the combined organic phases were washed with brine, dried with Na$_2$SO$_4$ and the solvent was removed under reduced pressure. The resulting residue was purified by FCC, eluting with 0-8% 2M NH$_3$ in MeOH/DCM. The obtained product was dissolved in MeCN (1 ml) and H$_2$O (1 ml) and an aqueous HCl solution (1M, 1 equivalent) was added. The mixture was lyophilized to afford the title compound (40%).

LCMS (Method 2): Rt 3.04 min, m/z 557 [MH$^+$].

$^1$H NMR (400 MHz, d-$_6$-DMSO with D$_2$O addition): 1.16 (9H, s), 1.75 (3H, s), 1.83-2.23 (7H, m), 2.90-3.10 (4H, m), 3.32-3.45 (1H, m), 3.54 (3H, s), 3.64-3.78 (1H, m), 4.82 (1H, dd, J=8.8, 5.7 Hz), 5.58-5.66 (1H, m), 6.00 (1H, s), 7.24-7.39 (6H, m), 7.82 (1H, d, J=10 Hz), 8.08-8.19 (1H, m).

General Procedure for Example 6

The compound in Table 2 was prepared starting from ((5-tert-butyl-2-methyl-2H-pyrazol-3-yl)-carbamic acid 2,2,2-trichloro-ethyl ester (WO 2013/083604, which is incorporated herein by reference in its entirety) and an appropriate amine using the procedure described to make Example 5.

incorporated herein by reference in its entirety, 113 mg, 0.29 mmol) and DIPEA (71 µl, 0.43 mmol) in dioxane (3 ml) was treated with (1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-ylamine (WO 2013/083604, which is incorporated herein by reference in its entirety, 112 mg, 0.29 mmol). The reaction mixture was heated at 50° C. for 3 days, cooled at RT and the volatiles were removed under reduced pressure. The crude was purified by HPLC (Gemini C18, 40-60% MeCN in H$_2$O, 0.1% NH$_4$OH, 18 ml/min). The obtained product was dissolved in MeCN (1 ml) and H$_2$O (1 ml) and an aqueous HCl solution (1M, 1 equivalent) was added. The mixture was lyophilized to afford the title compound (95 mg, 60%).

NB. The hydrochloride salt presented two different stereoisomers due to formation of a stereogenic centre on the ammonium and the stereoisomers have been labelled with $^\#$.

LCMS (Method 2): Rt 3.53 min, m/z 558 [MH$^+$].

$^1$H NMR (400 MHz, d$_6$-DMSO): 1.00-1.30 (1514, m), 1.80-2.70 (814, m), 3.00-3.80 (3H, m), 4.85-4.95 (1H, m), 5.40-5.60 (1.7H$^\#$, m), 5.85-5.92 (0.3H$^\#$, m), 6.37 (1H, s), 7.00-7.11 (1H, m), 7.25-7.42 (5H, m), 7.83 (1H, d, J=10 Hz), 8.47 (0.7H$^\#$, br s), 8.85 (0.3H$^\#$, br s), 9.30-9.40 (1H, m), 10.37 (0.7H$^\#$, br s), 11.82 (0.3H$^\#$, br s).

TABLE 2

| Ex. | Amine-Intermediate | Structure | NMR (400 MHz) δ | LC-MS |
|---|---|---|---|---|
| 6 | (1S,4R)-4-[3-(1-dimethylamino-1-methyl-ethyl)-[1,2,4]triazolo[4,3-a]pyridin-6-yloxy]-1,2,3,4-tetrahydro-naphthalen-1-ylamine (WO 2013/083604, which is incorporated herein by reference in its entirety) | 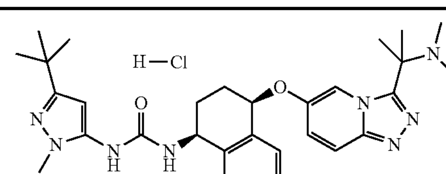 | $^1$H NMR (400 MHz, d-$_6$-DMSO): 1.20 (9H, s), 1.86-2.25 (10H, m), 2.63-2.86 (6H, m), 3.60 (3H, s), 4.83-4.92 (1H, m), 5.73-5.89 (1H, m), 6.05 (1H, s), 7.07 (1H, d, J = 8.5Hz), 7.30 (1H, dt, J = 1.9, 6.9Hz), 7.35-7.43 (4H, m), 7.88 (1H, d, J = 9.7Hz), 8.54-8.62 (1H, m), 8.65 (1H, d, J = 1.4 Hz), 11.05-11.20 (1H, br) | (Method 2): Rt 3.06 min, m/z 545.3 [MH$^+$]. |

Example 7

1-(5-tert Butyl-isoxazol-3-yl)-3-{(1S,4R)-4-[3-((S)-1-isopropyl-pyrrolidin-2-yl)-[1,2,4]triazolo[4,3-a]pyridine-6-yloxy]-1,2,3,4-tetrahydronaphthalen-1-yl}-urea hydrochloride salt

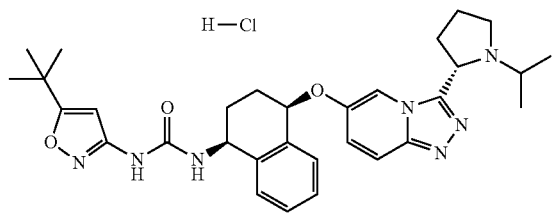 [SMILES: CC(C)N1CCC[C@H]1c1nnc2ccc(O[C@@H]3CC[C@H](NC(=O)Nc4cc(C(C)(C)C)on4)c4ccccc43)cn12 ; Cl]

A stirred solution of (5-tert-butyl-isoxazol-3-yl)-carbamic acid 2,2,2-trichloro-ethyl ester (WO 2013/083604, which is Example 8

1-(5-tert Butyl-isoxazol-3-yl)-3-{(1S,4R)-4-[3-((S)-1-methyl-pyrrolidin-2-yl)-[1,2,4]triazolo[4,3-a]pyridine-6-yloxy]-1,2,3,4-tetrahydronaphthalen-1-yl}-urea hydrochloride salt

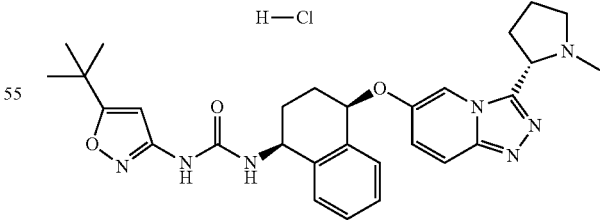

A stirred solution of (5-tert-butyl-isoxazol-3-yl)-carbamic acid 2,2,2-trichloro-ethyl ester (WO 2013/083604, which is incorporated herein by reference in its entirety, 115 mg, 0.36 mmol) and DIPEA (80 µl, 0.46 mmol) in dioxane (3.3 ml) was treated with (1S,4R)-4-[3-((S)-1-methyl-pyrrolidin-2-yl)- [1,2,4]triazolo[4,3-a]pyridin-6-yloxy]-1,2,3,4-tetrahydro-naphthalen-1-ylamine (WO 2013/083604, which is incorporated herein by reference in its entirety, 110 mg, 0.30 mmol). The reaction mixture was heated at 60° C. for 3 days, cooled at RT and the volatiles were removed under reduced pressure. The crude was purified by FCC, eluting with 0-10% 2M NH$_3$ in MeOH/DCM, followed by MDAP (Method 3). The obtained product was dissolved in MeCN (1 ml) and H$_2$O (1 ml) and an aqueous HCl solution (1M, 1 equivalent) was added. The mixture was lyophilized to afford the title compound (47 mg, 30%).

NB. The hydrochloride salt presented two different stereoisomers due to formation of a stereogenic centre on the ammonium and the stereoisomers have been labelled with #.

LCMS (Method 2): Rt 3.41 min, m/z 530 [MH$^+$].

$^1$H NMR (400 MHz, d$_6$-DMSO): 1.23 (9H, s), 1.80-2.50 (8H, m), 2.63-2.77 (1H, m), 2.86 (2H, s), 3.20-3.30 (1H, m), 3.65-3.78 (1H, m), 4.85-4.94 (1H, m), 5.31-5.40 (0.7H$^\#$, m), 5.50-5.70 (1.3H$^\#$, m), 6.35 (1H, s), 7.02-7.12 (1H, m), 7.24-7.40 (5H, m), 7.81 (1H, d, J=10 Hz), 8.46 (0.7H$^\#$, br s), 8.80 (0.3H$^\#$, br s), 9.27-9.38 (1H, m), 10.65 (0.7H$^\#$, br s), 11.64 (0.3H$^\#$, br s).

Biological Assays

P38alpha Enzyme Inhibition Assay

The inhibitory activity of compounds was determined using an Alphascreen® (Perkin Elmer) based kinase activity assay. Kinase reactions consisted of 25 mM HEPES pH 7.5, 10 mM MgCl$_2$, 100 μM Na$_3$VO$_4$, 2 mM DTT, 0.05 mg/ml Tween 20, 100 pM p38alpha (Invitrogen, PV3304), 1% DMSO and 0.3 μg/ml ATF-2 fusion protein (New England Biolabs, 9224). Compounds were incubated under these conditions for 2 hours, at 25° C., prior to the initiation of the kinase activity by the addition of the 250 μM ATP. Reaction volumes were 20 uL. After 1 hr at 25° C. reactions were stopped by the adding 10 uL of 25 mM HEPES pH 7.5 containing 62.5 mM EDTA, 0.05% Triton X-100, 10% BSA and 0.83 ng/uL anti-phospho-ATF2 antibody (Abcam, ab28812). Detection was performed by measuring luminescence following the addition of Alphascreen Donor beads (Perkin Elmer 6765300) and Protein A Alphascreen Acceptor beads (Perkin Elmer 6760137), both at a final concentration of 20 ug/ml. IC$_{50}$ values were determined from concentration-response curves.

The compounds of the invention show p38a potencies (IC$_{50}$ values)<5 nM

LPS-Stimulated PBMC TNFα Release Assay

Peripheral Blood Mononuclear Cells (PBMCs) were isolated from healthy human volunteer blood using a standard density gradient centrifugation technique. Citrated blood was placed onto Histopaque™ and centrifuged. The PBMCs were removed from the density gradient interface and washed in phosphate buffered saline (PBS). The PBMCs were suspended in RPMI 1640 medium (without serum), dispensed into a 96-well plate and incubated at 37° C. for 3 h in a humidified incubator. After incubation, the medium was replaced (with medium containing 1% foetal bovine serum) and the plate incubated at 37° C., for 1 h, in the presence of test compound or the appropriate vehicle. LPS (10 ng/ml), or an appropriate vehicle control, was then added to the cells and the plate returned to the incubator for 18 h. Cell-free supernatants were removed and assayed for TNFα levels using MSD plates on the Sector Imager 6000 (MesoScale).

A dose response curve to each test compound was performed and the effect of compound in each experiment was expressed as a percentage inhibition of the control TNFα release. Dose response curves were plotted and compound potency (IC$_{50}$) was determined. Compounds were tested in at least three separate experiments.

The compounds of the invention show human PBMC potencies (IC$_{50}$ values)<2 nM.

TNFα-Stimulated BEAS-2B IL-8 Release Assay

The BEAS-2B cells are Bronchial Epithelial cells and it is known in the literature that this cell line releases IL-8 upon stimulation with TNFα (see Chmura K, Bai X, Nakamura M, Kandasamy P, McGibney M, Kuronuma K, Mitsuzawa H, Voelker D R, Chan E D. Am J Physiol Lung Cell Mol Physiol. 2008; 295(1):L220-30; King E M, Holden N S, Gong W, Rider C F, Newton R. J Biol Chem. 2009; 284(39):26803-15; Carta S, Silvestri M, and Giovanni A Ital J Pediatr. 2013; 39: 29, all of which are incorporated herein by reference in their entireties) and p38 inhibitors inhibit the release of IL-8 in TNFα stimulated BEAS-2B cells (see King E M, Holden N S, Gong W, Rider C F, Newton R. J Biol Chem. 2009; 284(39):26803-15, which is incorporated herein by reference in its entirety).

Human bronchial epithelial cell line BEAS-2B was purchased from Sigma (St. Louis, Mo.). BEAS-2B cells were cultured in Bronchial Epithelial cell Growth Medium (BEGM), prepared by supplementing Bronchial Epithelial Basal Medium with SingleQuotes™ (Lonza, Switzerland), which contains retinoic acid, epidermal growth factor, epinephrine, transferrin, triiodothyronin, insulin, hydrocortisone, antimicrobial agents, and bovine pituitary extract. In addition, BEGM medium was supplemented with 2 mM glutamine, 100 U penicillin and 100 μg/ml streptomycin (Life Technologies), in an atmosphere of 95% air and 5% CO2 at 37° C.

BEAS-2B were seeded in 48-well plates at the density of 3×104 cells per well, grown to approximately 80-90% confluence. Cells were pre-incubated with p38 inhibitors for 1 hour and then stimulated with TNF-α (10 ng/ml) for 18 h at 37° C. with 5% CO2. Subsequently, supernatants were collected and used for measuring IL-8 levels using a paired antibody quantitative ELISA kit purchased from Life Technologies (detection limit: 5 pg/ml). All the treatments were perfomted at least in quadruplicate.

A concentration-response curve to each test compound was performed and the effect of compound in each experiment was expressed as a percentage inhibition of the control IL-8 release. Compound potency (IC$_{50}$) was calculated by the analysis of the sigmoidal dose-response curve (variable slope) elaborated by Graph Pad PRISM4 program.

The compounds of the invention show BEAS-2B potencies (IC$_{50}$ values)<0.8 nM.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

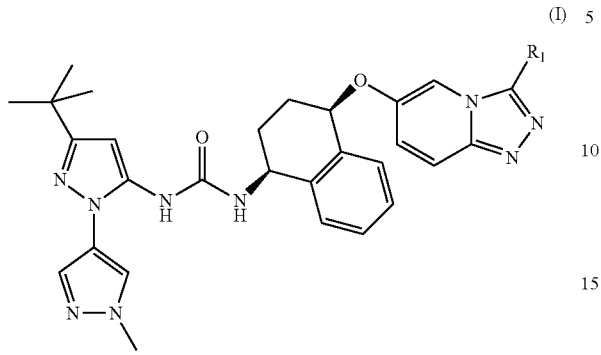

wherein
R₁ is a group of one of the following formulae:

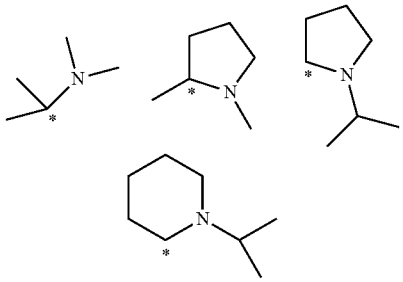

or a pharmaceutically acceptable salt thereof.
2. A compound or pharmaceutically acceptable salt according to claim 1, which is:
- 1-(3-tert-Butyl-1'-methyl-1'H-[1,4']bipyrazolyl-5-yl)-3-{(1S,4R)-4-[3-(1-dimethylamino-1-methyl-ethyl)-[1,2,4]triazolo[4,3-a]pyridin-6-yloxy]-1,2,3,4-tetrahydronaphthalenyl}-urea hydrochloride salt;
- 1-(3-tert-Butyl-1'-methyl-1'H-[1,4']bipyrazolyl-5-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydronaphthalenyl}-urea hydrochloride salt;
- 1-(3-tert-Butyl-1'-methyl-1'H-[1,4']bipyrazolyl-5-yl)-3-{(1S,4R)-4-[3-((S)-1-isopropyl-pyrrolidin-2-yl)-[1,2,4]triazolo[4,3-a]pyridin-6-yloxy]-1,2,3,4-tetrahydronaphthalenyl}-urea hydrochloride salt; or
- 1-(3-tert-Butyl-1'-methyl-1'H-[1,4']bipyrazolyl-5-yl)-3-{(1S,4R)-4-[3-((S)-1-isopropyl-piperidin-2-yl)-[1,2,4]triazolo[4,3-a]pyridin-6-yloxy]-1,2,3,4-tetrahydronaphthalen-1-yl}-urea hydrochloride salt.

3. A compound of formula (II):

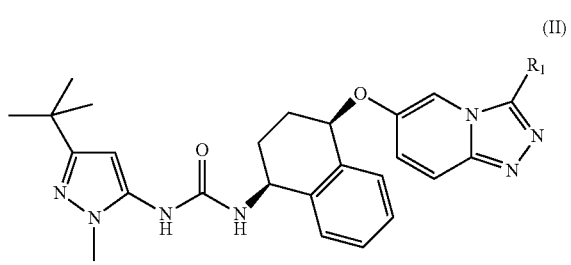

wherein
R₁ is a group of one of the following formulae:

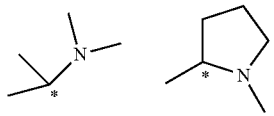

or a pharmaceutically acceptable salt thereof.
4. A compound or pharmaceutically acceptable salt according to claim 3, which is:
- 1-(5-tert-Butyl-2-methyl-2H-pyrazol-3-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea hydrochloride salt; or
- 1-(5-tert-Butyl-2-methyl-2H-pyrazol-3-yl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea hydrochloride salt.

5. A compound of formula (III):

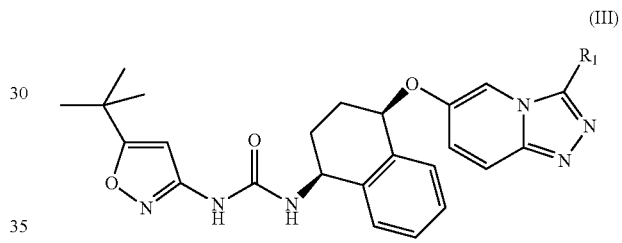

wherein
R₁ is a group of one of the following formulae:

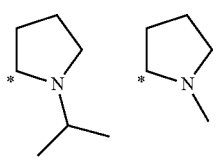

or a pharmaceutically acceptable salt thereof.
6. A compound or pharmaceutically acceptable salt according to claim 5, which is:
- 1-(5-tert Butyl-isoxazol-3-yl)-3-{(1S,4R)-4-[3-((S)-1-isopropyl-pyrrolidin-2-yl)-[1,2,4]triazolo[4,3-a]pyridine-6-yloxy]-1,2,3,4-tetrahydronaphthalen-1-yl)}-urea hydrochloride salt; or
- 1-(5-tert Butyl-isoxazol-3-yl)-3-{(1S,4R)-4-[3-((S)-1-methyl-pyrrolidin-2-yl)-[1,2,4]triazolo[4,3-a]pyridine-6-yloxy]-1,2,3,4-tetrahydronaphthalen-1-yl}-urea hydrochloride salt.

7. A pharmaceutical composition, comprising a compound or a pharmaceutically acceptable salt according to claim 1 and one or more pharmaceutically acceptable carriers.

* * * * *